(12) United States Patent
Hong et al.

(10) Patent No.: US 11,892,713 B2
(45) Date of Patent: *Feb. 6, 2024

(54) OPHTHALMIC LENS HAVING MORPHED SINUSOIDAL PHASE SHIFT STRUCTURES

(71) Applicant: Alcon Inc., Fribourg (CH)

(72) Inventors: Xin Hong, Fort Worth, TX (US); William Andrew Maxwell, Fresno, CA (US); Xin Wei, Frisco, TX (US)

(73) Assignee: Alcon Inc., Fribourg (CH)

( * ) Notice: Subject to any disclaimer, the term of this patent is extended or adjusted under 35 U.S.C. 154(b) by 511 days.

This patent is subject to a terminal disclaimer.

(21) Appl. No.: 16/950,456

(22) Filed: Nov. 17, 2020

(65) Prior Publication Data

US 2021/0063767 A1     Mar. 4, 2021

Related U.S. Application Data

(63) Continuation of application No. 16/043,457, filed on Jul. 24, 2018, now Pat. No. 10,871,659.

(60) Provisional application No. 62/536,044, filed on Jul. 24, 2017.

(51) Int. Cl.
  *G02C 7/02* (2006.01)
  *G02C 7/04* (2006.01)
  *A61F 2/16* (2006.01)

(52) U.S. Cl.
  CPC ............. *G02C 7/028* (2013.01); *A61F 2/164* (2015.04); *A61F 2/1618* (2013.01); *G02C 7/022* (2013.01); *G02C 7/04* (2013.01); *G02C 7/041* (2013.01); *G02C 7/044* (2013.01); *G02C 7/049* (2013.01); *A61F 2/1654* (2013.01)

(58) Field of Classification Search
  CPC ........ G02C 7/022; G02C 7/024; G02C 7/028; G02C 7/06; G02C 7/061; G02C 7/063; G02C 7/065; G02C 7/066; G02C 7/068; A61F 2/1618; A61F 2/1637; A61F 2/164; A61F 2/1645; A61F 2/1654
  USPC ........................................ 351/159.01–159.77
  See application file for complete search history.

(56) References Cited

U.S. PATENT DOCUMENTS

| 4,995,714 | A | | 2/1991 | Cohen | |
|---|---|---|---|---|---|
| 5,760,871 | A | * | 6/1998 | Kosoburd | A61F 2/1613 359/569 |
| 6,923,539 | B2 | * | 8/2005 | Simpson | A61F 2/1613 351/159.2 |
| 8,241,354 | B2 | * | 8/2012 | Hong | G02C 7/042 623/6.27 |
| 10,871,659 | B2 | * | 12/2020 | Hong | G02C 7/022 |
| 2006/0007394 | A1 | * | 1/2006 | Shirayanagi | G02C 7/02 351/159.74 |
| 2010/0016961 | A1 | | 1/2010 | Hong | |

(Continued)

FOREIGN PATENT DOCUMENTS

EP     2813881 A1    12/2014

*Primary Examiner* — Nicholas R. Pasko

(57) ABSTRACT

An ophthalmic lens includes an optic comprising an anterior surface, a posterior surface, and an optical axis. At least one of the anterior surface and the posterior surface has a surface profile including a base curvature and a plurality of morphed sinusoidal phase shift structures. The base curvature may correspond to a base optical power of the ophthalmic lens, and the morphed sinusoidal phase shift structures may be configured to extend depth of focus of the ophthalmic lens at intermediate or near viewing distances.

10 Claims, 6 Drawing Sheets

(56) References Cited

U.S. PATENT DOCUMENTS

2014/0009736 A1* 1/2014 Zhao .................... A61F 2/1654
                                                                                          351/159.01
2017/0273781 A1* 9/2017 Zhao ........................ G02C 7/00

\* cited by examiner

OPHTHALMIC LENS HAVING MORPHED SINUSOIDAL PHASE SHIFT STRUCTURES

PRIORITY CLAIM

This application is a continuation of U.S. Non-Provisional application Ser. No. 16/043,457 filed Jul. 24, 2018 and claims the benefit of priority of U.S. Provisional Patent Application Ser. No. 62/536,044 titled "OPHTHALMIC LENS HAVING MORPHED SINUSOIDAL PHASE SHIFT STRUCTURES," filed on Jul. 24, 2017, whose inventors are Xin Hong, William Andrew Maxwell and Xin Wei, both of which are hereby incorporated by reference in its entirety as though fully and completely set forth herein.

FIELD

This present disclosure relates generally ophthalmic lenses and, more particularly, to ophthalmic lenses having extended depth of focus to increase pseudo-accommodation for intermediate and near vision.

BACKGROUND

Cataract surgery is one of the most common ophthalmic surgeries and involves the replacement of the cataractous crystalline lens with an artificial intraocular lens (IOL). Typically, a monofocal intraocular lens (with a fixed focal length) is placed in the capsular bag to provide the best distance vision. While patients implanted with monofocal IOLs have good distance vision, quality of vision at intermediate and near is often insufficient to support activities of daily living. Specifically, a good continuous range of vision at near has become increasingly significant to patients because of daily tasks related to computers, mobile devices and other technologic advances. Accordingly, there is a need for an IOL, as well as contact lenses, to provide an extended and continuous range of functional vision at intermediate/near viewing distances.

SUMMARY

The present disclosure generally concerns multifocal ophthalmic lenses (e.g., IOLs, rigid and soft contact lenses, etc.) that provide both satisfactory distance vision and that extend the depth-of-focus at a range of intermediate to near viewing distances. In certain embodiments, an ophthalmic lens includes an optic comprising an anterior surface, a posterior surface, and an optical axis. At least one of the anterior surface and the posterior surface comprise a surface profile including a base curvature and a morphed sinusoidal phase shift (MSPS) structure. The base curvature may correspond to a base optical power of the ophthalmic lens, and the morphed sinusoidal phase shift structure may be configured to extend depth of focus of the ophthalmic lens at intermediate or near viewing distances and may comprise morphed sinusoidal phase shift zones.

In certain variants, the morphed sinusoidal phase shift structures are configured to extend depth of focus at intermediate or near viewing distances in the range of 30-55 cm or 33-50 cm.

The surface profile of the lens may be defined as:

$$Z_{optic} = Z_{base} + Z_{MSPS}$$

wherein $Z_{base}$ defines the surface profile of the base curvature and $Z_{MSPS}$ defines the plurality of morphed sinusoidal phase shift structures.

Further, $Z_{base}$ may be defined as $$Z_{base}(r) = \frac{cr^2}{1+\sqrt{1-(1+k)c^2r^2}} + a_2r^2 + a_4r^4 + a_6r^6 + a_8r^8 + a_{10}r^{10} + a_nr^n \ldots + a_nr^n$$

where r denotes a radial distance from the optical axis, c denotes a base curvature of the surface, k denotes a conic constant, and $a_2$, $a_4$, and $a_6$ are, respectively, second, fourth, and sixth order coefficients.

Additionally, $Z_{MPSS}$ may be defined as:

$$Z_{MSPS}(r) = M_i \frac{T_i^P}{\pi}\left(1 - \cos\left(\frac{r-R_i}{T_i^P}\pi\right)\right), R_i \le r < R_i + T_i^P$$

$$Z_{MSPS}(r) = M_i \frac{T_i^P}{\pi}\left(1 - \cos\left(\frac{r-R_i-T_i^P}{R_{i+1}-R_i-T_i^P}\pi + \pi\right)\right),$$

$$R_i + T_i^P \le r < R_{i+1}$$

where r denotes a radial distance from the optical axis, $R_i$ and $R_{i+1}$ are the starting and ending radial positions of each zone, $M_i$ are step heights of each zone, $T_i^P$ are the critical points within each zone, and i indicates zone numbers.

In certain embodiments, the present disclosure may provide one or more technical advantages. For example, embodiments of the disclosure combine a base monofocal aspheric curvature with a morphed sinusoidal phase shift structure to provide an extended range of functional vision at near and/or intermediate distances, while maintaining distance visual acuity and a safety profile similar to that of a typical monofocal lens. Using morphed sinusoidal phase shift structures may eliminate discontinuous diffractive structures and small aperture or pinhole effects found in conventional EDF designs. Accordingly, embodiments may enable patients to enjoy visual range superior to conventional EDF or monofocal designs with fewer visual disturbances, reduced loss of light, and greater efficiency.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

One skilled in the art will understand that the drawings, described below, are for illustration purposes only, and not intended to limit the scope of the disclosure.

DETAILED DESCRIPTION

The present disclosure generally concerns ophthalmic lenses (e.g., IOLs and contact lenses) that provide both satisfactory distance vision and extended depth-of-focus at ranges in intermediate to near viewing distances. More particularly, embodiments of the present disclosure provide an ophthalmic lens such as an IOL or contact lens having (1) a mono-focal aspheric lens to partially or completely correct patient's lower-order and/or higher-order aberrations at distances and (2) morphed sinusoidal phase shift (MSPS) structures added on anterior and/or posterior lens surfaces to extend the depth-of-focus at a range of intermediate-near viewing distances. Such MSPS-enhanced lens designs may provide an extended and continuous range of functional vision at intermediate/near viewing distances (e.g., from 50 cm to 33 cm) while maintaining distance visual acuity and a safety profile similar to that of a monofocal lens.

Figure 1A:
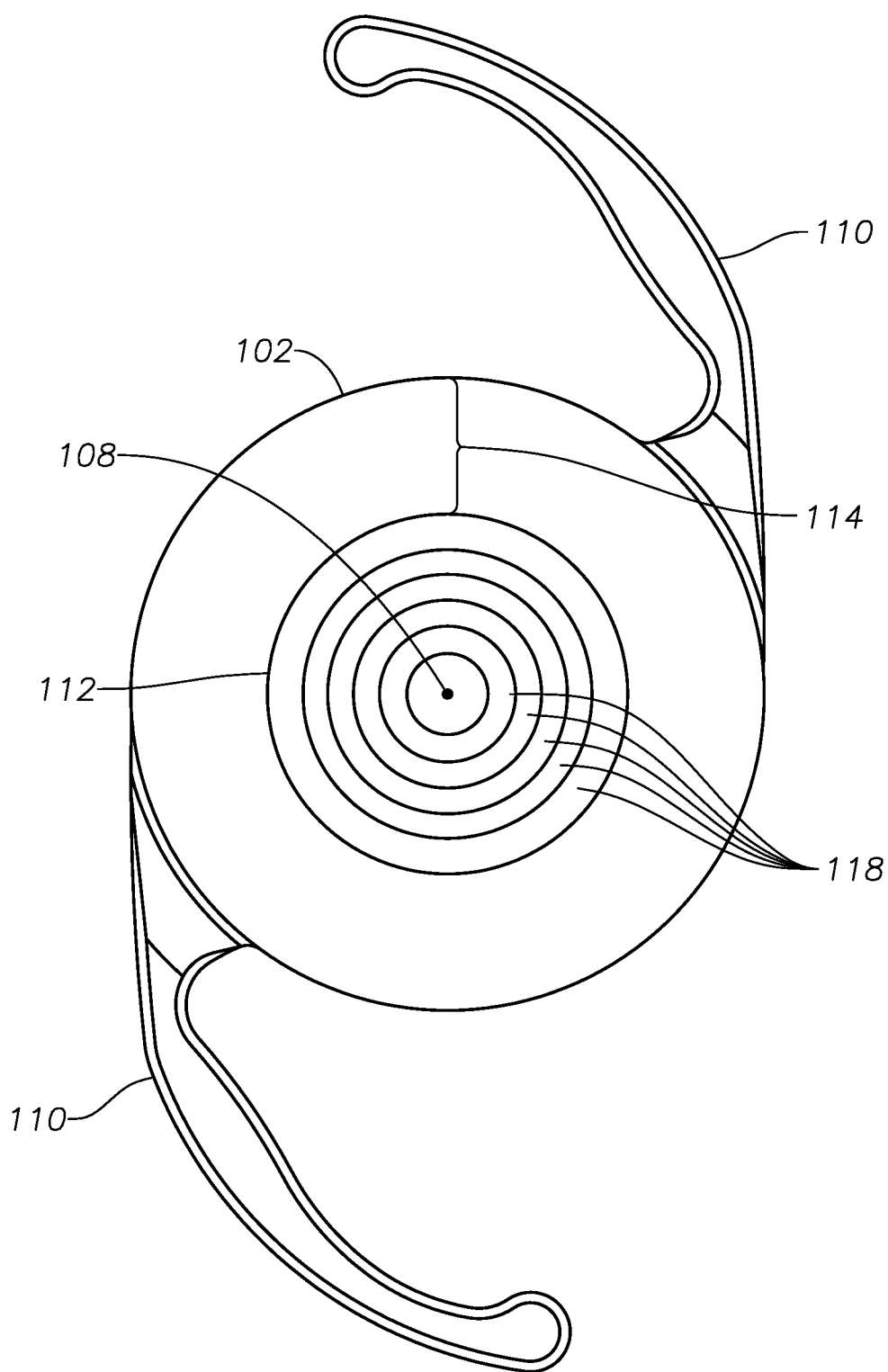
FIGS. 1A-1B illustrate an example embodiment of an extended depth of focus IOL having morphed sinusoidal phase shift structures, according to certain embodiments.
Figure 1B:
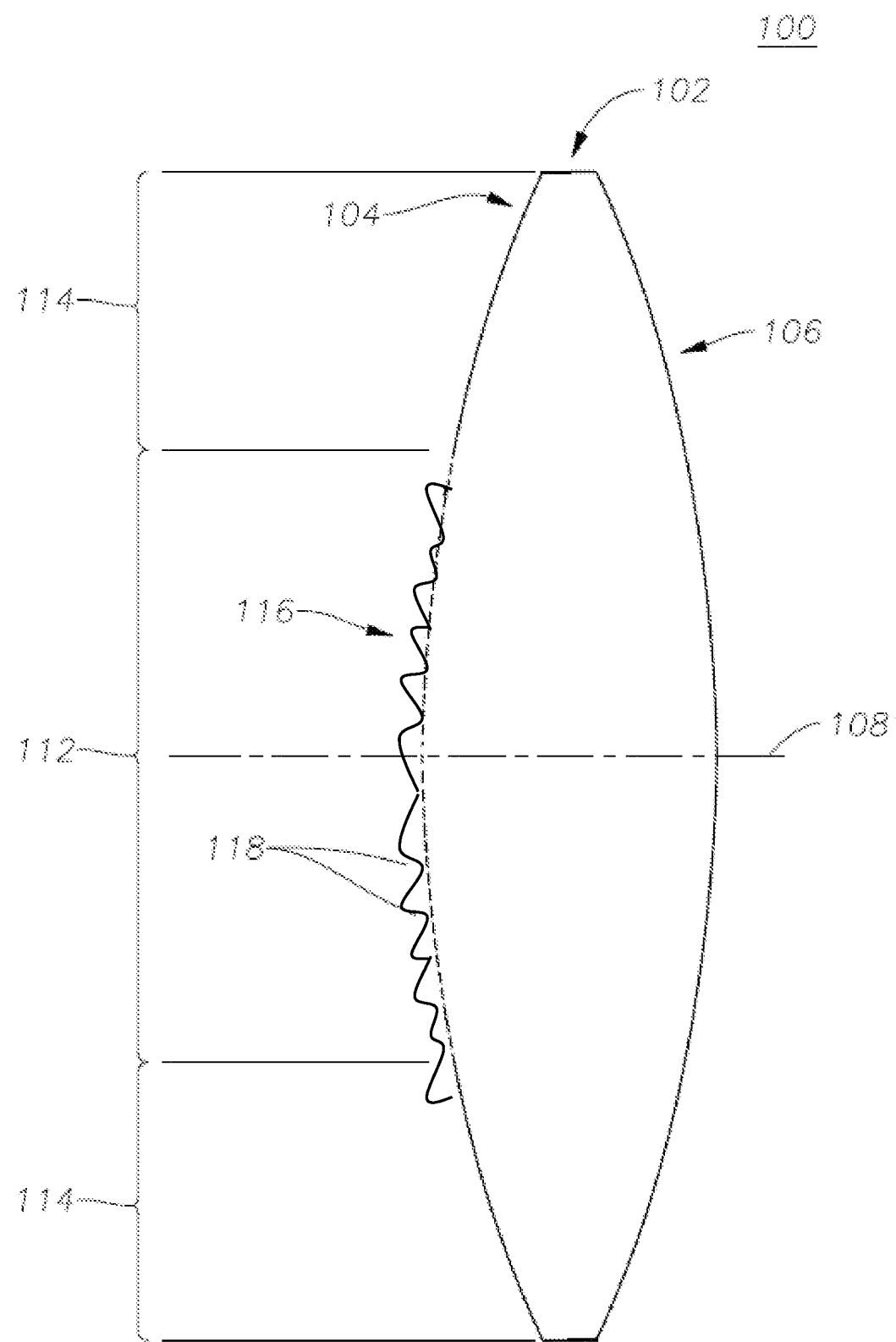

FIGS. 1A-1B illustrates an example embodiment of an IOL 100 having extended depth of focus for intermediate-near vision, according to certain embodiments. IOL 100 includes an optic 102 having an anterior surface 104 and a posterior surface 106 that are disposed about an optical axis 108. Optic 102 may be convex on both sides (biconvex) and made of a soft plastic that can be folded prior to insertion, allowing placement through an incision smaller than the optic diameter of the lens. IOL 100 may further include a plurality of haptics 110 generally operable to position and stabilize IOL 100 within the capsular bag of a patient's eye. Although haptics 110 having a particular structure are illustrated in FIG. 1, the present disclosure contemplates haptics 110 having any suitable shape and structure for stabilizing IOL 100 within the capsular bag, the ciliary sulcus, or any other suitable location within the eye.

The anterior surface 104 (or, in other embodiments, posterior surface 106) of optic 102 may have a base curvature corresponding to a base optical power of the IOL 100. The base optical power of IOL 100 typically corresponds to the distance vision of the patient. However, this is not required. For example, a non-dominant eye may have an IOL with a base optical power is slightly less than the corresponding distance power for the patient to improve overall binocular vision for both eyes. In certain embodiments, the base curvature may be aspheric. It is noted that, although the figures illustrate anterior surface 104 of optic 102 as having a particular surface profiles, features, and characteristics, the present disclosure contemplates that profiles, features, and characteristics may additionally or alternatively be located on posterior surface 106 of optic 102. Further, although the disclosed examples primarily discuss an aspheric monofocal base lens, the MSPS structures described herein may be combined with other base lens profiles. Accordingly, the disclosure is not limited to aspheric monofocal optics, but includes other variants which would be contemplated by one skilled in the art.

In addition to a base curvature, the anterior surface 104 (or, in other embodiments, posterior surface 106) of optic 102 may include a plurality of regions. For example, anterior surface 104 may include a MSPS region 112, which may extend from the optical axis 108 to a first radial boundary, and a refractive region 114, which may extend from the first radial boundary to a second radial boundary (e.g., the edge of the optic 102). Although anterior surface 104 of optic 102 is depicted and described as having two regions (MSPS region 112 and refractive region 114), the present disclosure contemplates that anterior surface 104 or posterior surface 106 of optic 102 may include a surface profile having any suitable number of regions. As just one example, anterior surface 104 could alternatively include a surface profile having two refractive regions separated by a diffractive region.

MSPS region 112 may comprise a morphed sinusoidal phase shift (MSPS) structure 116 having a plurality of MSPS features 118 (also known as zones). As described in detail below, the MSPS structure 116 may be added to a base curvature of a monofocal aspheric optic 102 to form an IOL which may provide pseudophakic patients with satisfying distance vision and continuous range of vision correction from intermediate to near distances (e.g., from 2D-3D, 1.5D-2.5D, 1.5D-3.0D).

The surfaces of an MSPS-enhanced optic 102 may be described mathematically. In particular, optic 102 may comprise a base aspheric mono-focal lens that corrects a patient's lower and/or higher aberrations at a distance and may have particular sag profile. Sag is an indication of the z-component of the displacement of the optical surface from the vertex at a radial distance r from the optical axis. The anterior and posterior surface sag profiles for the base lens ($Z_{base}$) of optic 102 can be described according to Equation (1):

$$Z_{base}(r) = \frac{cr^2}{1 + \sqrt{1 - (1+k)c^2 r^2}} + a_2 r^2 + a_4 r^4 + a_6 r^6 + a_8 r^8 + a_{10} r^{10} + \cdots + a_n r^n \quad \text{Eq. (1)}$$

Wherein,
r denotes a radial distance from the optical axis;
c denotes a base curvature of the surface;
k denotes a conic constant;
$a_s$ is a second order deformation constant;
$a_4$ is a fourth order deformation constant;
$a_6$ is a sixth order deformation constant.
$a_8$ is a eighth order deformation constant; and
$a_{10}$ is a tenth order deformation constant.

Figure 2:
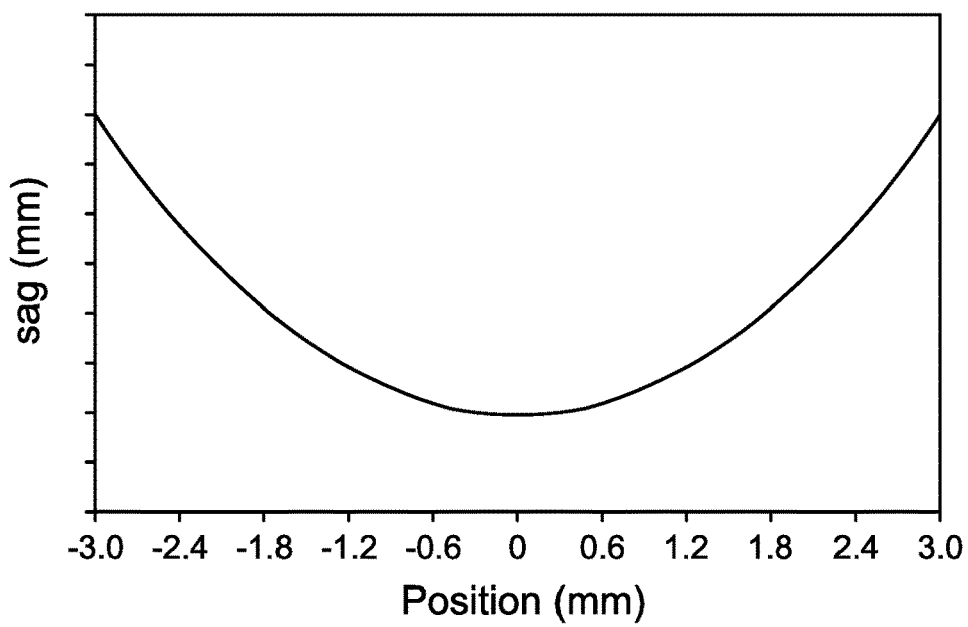
FIG. 2 illustrates an exemplary surface sag plot of a base monofocal optic.

FIG. 2 is a surface sag plot based on Equation (1). The curvature of anterior and posterior surfaces may be optimized such that the base lens corrects defocus of the patient's eye. Moreover, the conic constant (k) and higher-order coefficients (e.g., $a_2$, $a_4$, $a_6$, $a_8$ . . . ) can be adjusted to yield different levels of spherical aberration for the design of optic 102. Such spherical aberration, when combined with the corneal spherical aberration of an individual patient or an average patient population, can provide patients with optimal distance vision correction.

To extend depth of focus of the base lens at intermediate-near distances, a MSPS structure 116 comprising as plurality of MSPS zones 116 may be added to either anterior surface 104 or posterior surface 106 of optic 102. The anterior or posterior surface sag profiles added by the MSPS structure (Zack) can be described according to Equation (2):

$$Z_{MPSS}(r) = M_i \frac{T_i^P}{\pi} \left(1 - \cos\left(\frac{r - R_i}{T_i^P} \pi\right)\right), \quad R_i \leq r < R_i + T_i^P \quad \text{Eq. (2)}$$

$$Z_{MPSS}(r) = M_i \frac{T_i^P}{\pi} \left(1 - \cos\left(\frac{r - R_i - T_i^P}{R_{i+1} - R_i - T_i^P} \pi + \pi\right)\right),$$

$$R_i + T_i^P \leq r < R_{i+1}$$

Wherein, r denotes a radial distance from the optical axis;
$R_i$ and $R_{i+1}$ are the starting and ending radial positions of each zone;
$M_i$ are step heights of each zone;
$T_i^P$ are the critical points within each zone;
i indicates zone numbers i=0, 1, 2, 3 . . . .

Figure 3:
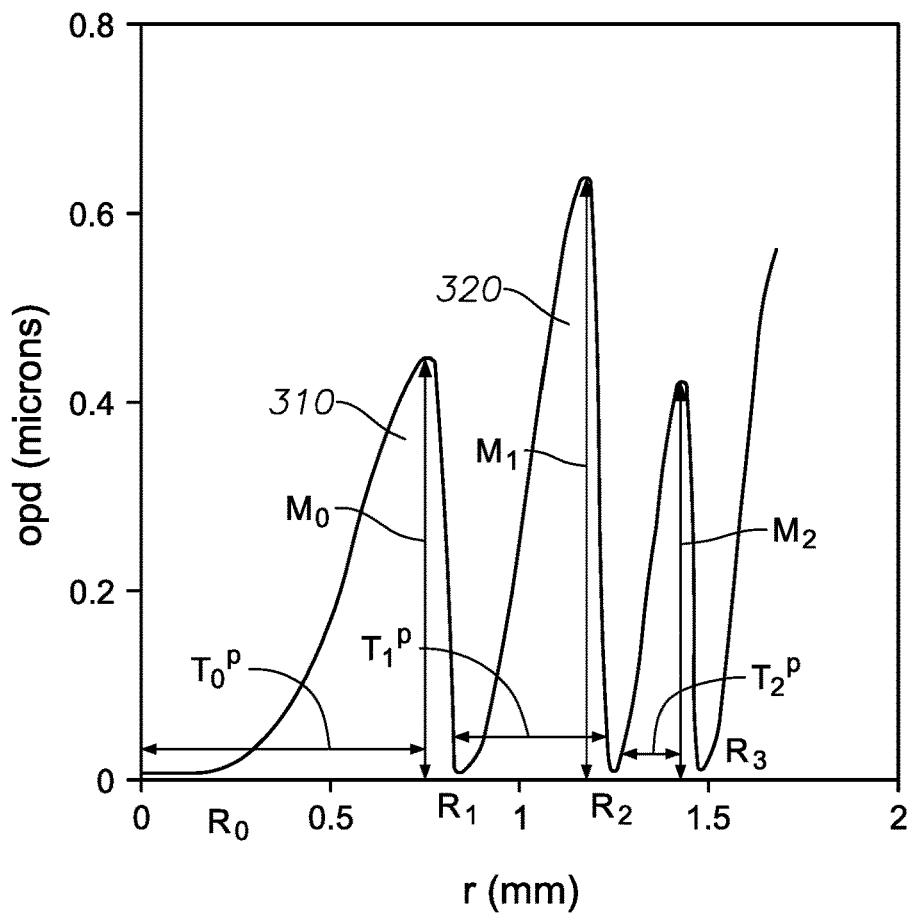
FIG. 3 illustrates an example of added surface sag resulting from multiple morphed sinusoidal phase shift structures on an optic.

FIG. 3 plots an example of added surface sag based on Equation (2). As can be seen in the curve on the left side of FIG. 3, a first sinusoidal phase shift zone 310 (i=0) spans from $R_0$ to $R_1$. $M_0$ is the step height of zone 310 and $T_0^P$ is the critical point corresponding to the radial distance of the peak of zone 310 (at point $M_0$) from $R_0$. A second sinusoidal phase shift zone 320 (i=1) spans from $R_1$ to $R_2$. $M_1$ is the step height of zone 320 and $T_1^P$ is the critical point corresponding to the radial distance of the peak of zone 320 (at point $M_1$) from $R_1$. This pattern continues in an analogous manner for additional zones.

The total sag of optic 102 ($Z_{optic}$) is a combination of base surface sag $Z_{base}$ with morphed sinusoidal phase shift structure 116 described by $Z_{MPSS}$ and may be described according to Equation (3) below:

$$Z_{optic} = Z_{base} + Z_{MSPS} \qquad \text{Eq. (3)}$$

Accordingly, a variety of improved optical designs may be developed by adding a MSPS structure to an aspheric monofocal base lens. In one example, morphed MSPS 116 comprises seven MSPS zones (i=0-6) as shown in Table 1, below:

TABLE 1

| Zone No. (i) | 0 | 1 | 2 | 3 | 4 | 5 | 6 |
|---|---|---|---|---|---|---|---|
| $R_{i+1} - R_i$ (mm) | 0.56 | 0.39 | 0.35 | 0.46 | 0.39 | 0.49 | 0.45 |
| $T_i^P/(R_{i+1} - R_i)$ | 0.56 | 0.79 | 0.87 | 0.56 | 0.75 | 0.64 | 0.82 |
| $M_i$ (μm) | 0.20 | 0.31 | 0.16 | 0.12 | 0.12 | 0.24 | 0.33 |

Figure 4A:
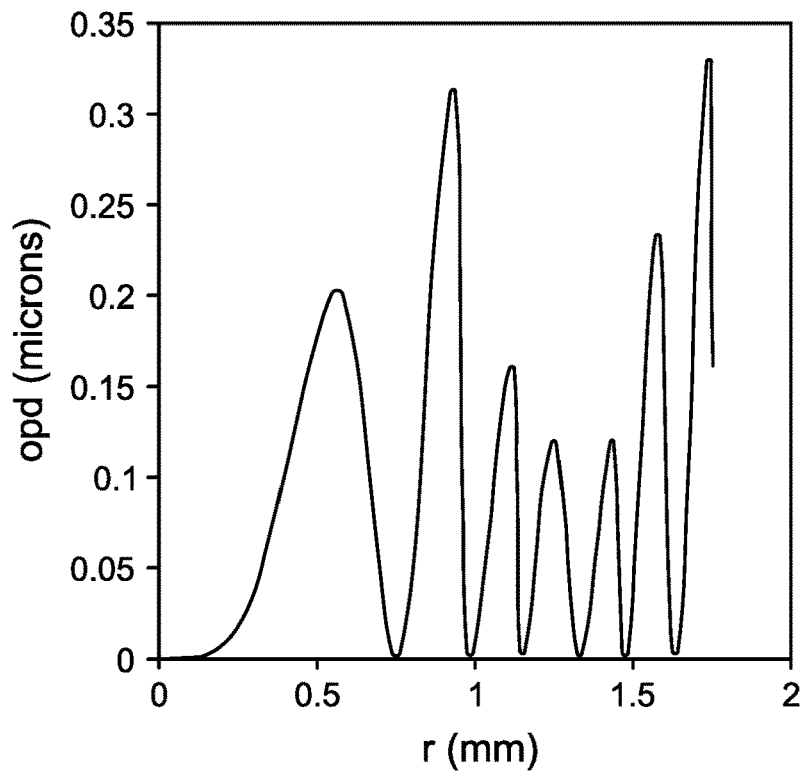
FIGS. 4A and 4B illustrate characteristics of an optic, according to certain embodiments.
Figure 4B:
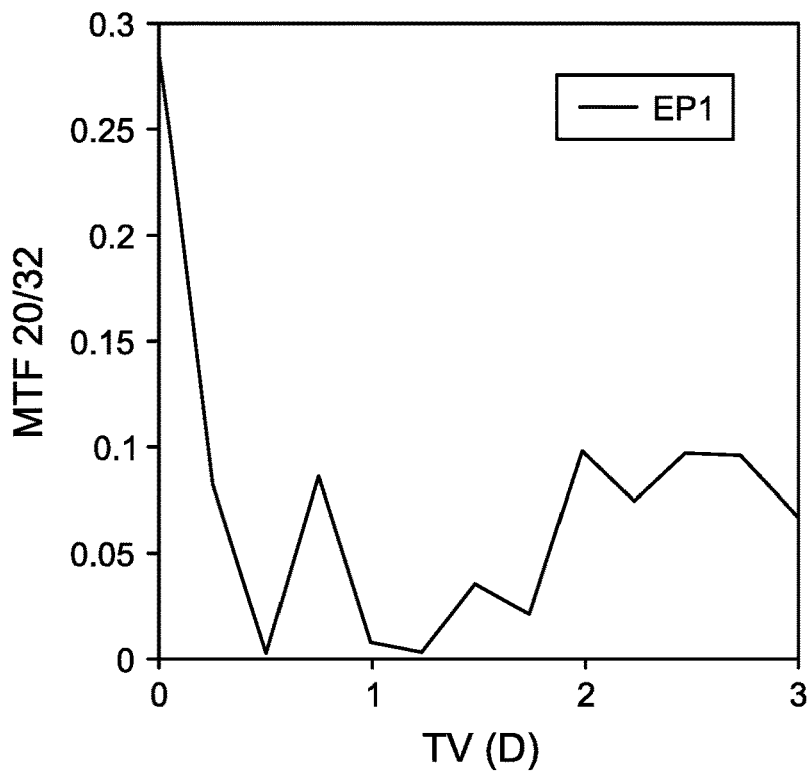

An optic 102 which includes a MSPS structure 116 in accordance with the parameters of Table 1 may provide extended depth of focus between 2D and 3D. Optical path delay (opd, as a function of radial distance in millimeters) and through-focus modular transfer function (MTF, as a function of target vergence (TV(D)) curves for a 3.4 mm entrance pupil (EP) and the parameters of Table 1 are plotted in FIGS. 4A and 4B.

In another example, MSPS structure 116 comprises seven MSPS zones (i=0-6) as shown in Table 2, below:

TABLE 2

| Zone No. (i) | 0 | 1 | 2 | 3 | 4 | 5 | 6 |
|---|---|---|---|---|---|---|---|
| $R_{i+1} - R_i$ (mm) | 0.43 | 0.40 | 0.41 | 0.27 | 0.48 | 0.56 | 0.59 |
| $T_i^P/(R_{i+1} - R_i)$ | 0.81 | 0.64 | 0.51 | 0.66 | 0.90 | 0.64 | 0.63 |
| $M_i$ (μm) | 0.25 | 0.15 | 0.14 | 0.28 | 0.25 | 0.22 | 0.29 |

Figure 5A:
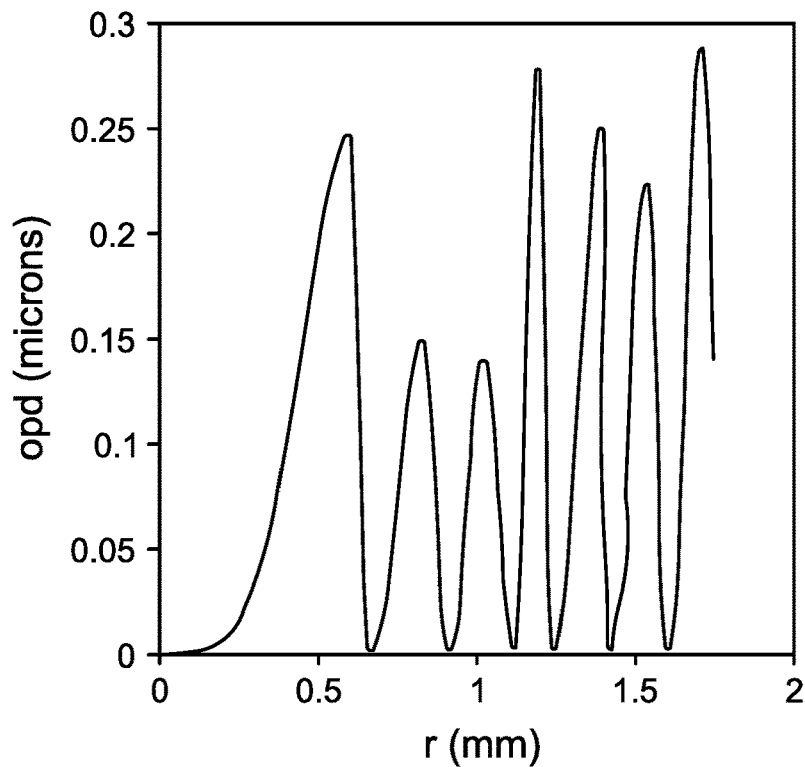
FIGS. 5A and 5B illustrate characteristics of an optic, according to certain embodiments.
Figure 5B:
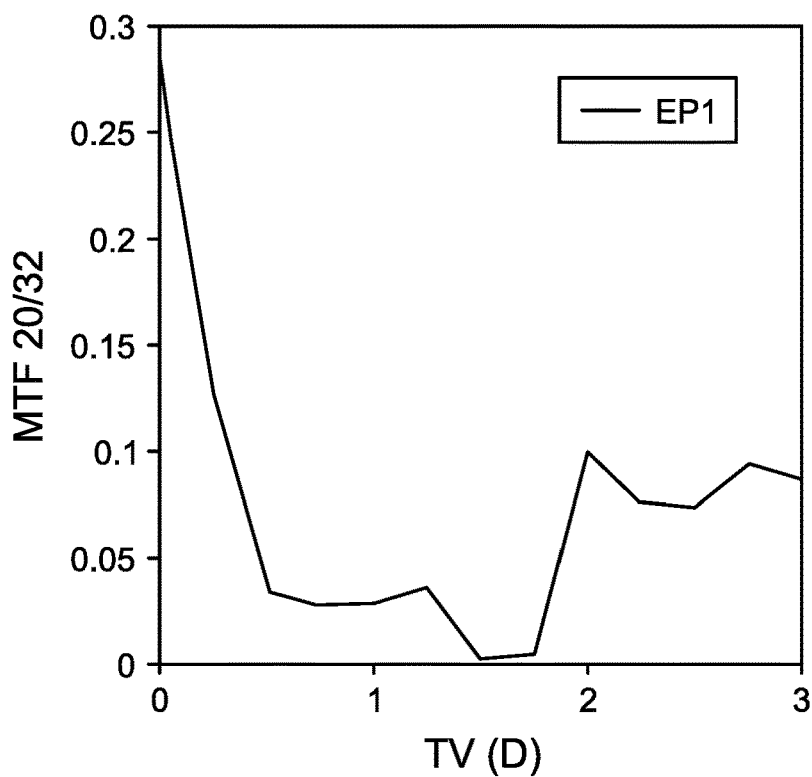

An optic 102 which includes a MSPS structure 116 in accordance with the parameters of Table 2 may provide extended depth of focus between 2D and 3D. Optical path delay (opd) and through-focus modular transfer function (MTF) curves for a 3.4 mm entrance pupil (EP) and the parameters of Table 2 are plotted in FIGS. 5A and 5B.

In another example, MSPS structure 116 comprises seven MSPS zones (i=0-6) as shown in Table 3, below:

TABLE 3

| Zone No. (i) | 0 | 1 | 2 | 3 | 4 | 5 | 6 |
|---|---|---|---|---|---|---|---|
| $R_{i+1} - R_i$ (mm) | 0.56597 | 0.56263 | 0.55974 | 0.5578 | 0.35399 | 0.47423 | 0.59278 |
| $T_i^P/(R_{i+1} - R_i)$ | 0.53174 | 0.89869 | 0.72774 | 0.70043 | 0.66239 | 0.80014 | 0.50225 |
| $M_i$ (μm) | 0.14009 | 0.31403 | 0.12667 | 0.13384 | 0.35788 | 0.16124 | 0.39076 |

Figure 6A:
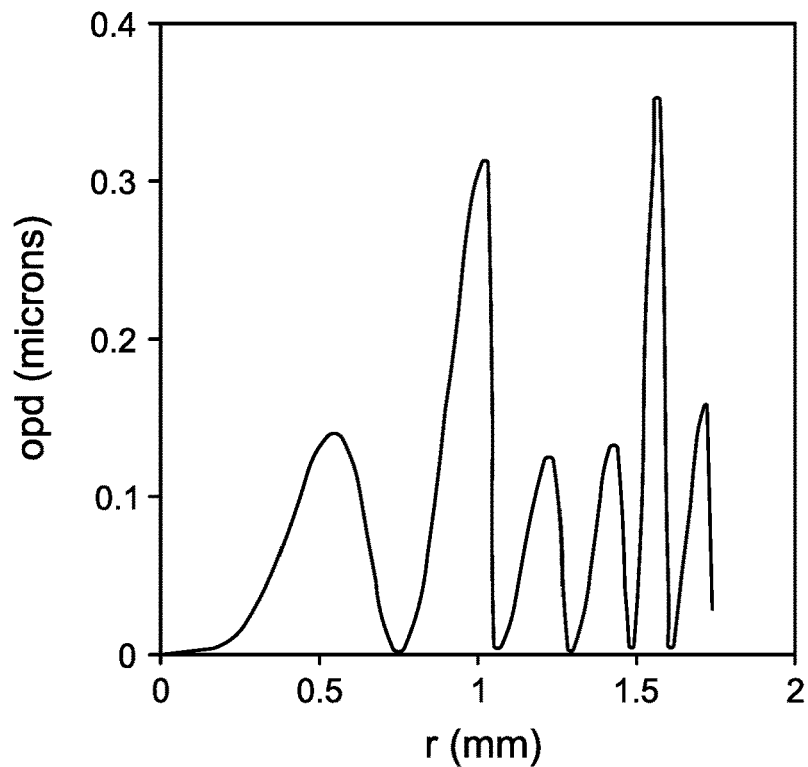
FIGS. 6A and 6B illustrate characteristics of an optic, according to certain embodiments.
Figure 6B:
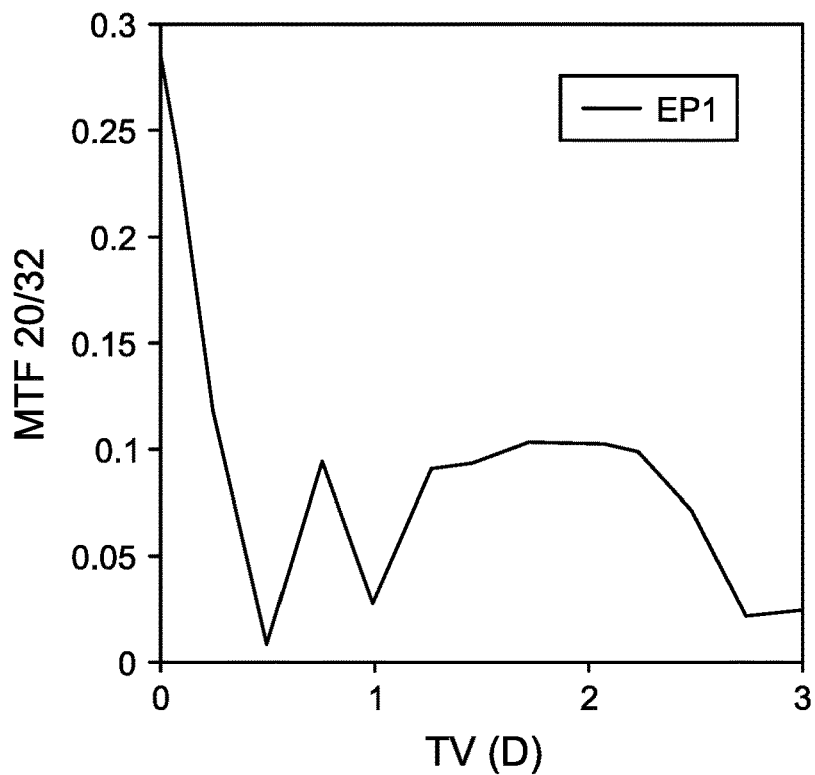

An optic 102 which includes a MSPS structure 116 in accordance with the parameters of Table 3 may provide extended depth of focus between 1.5D and 2.5D. Optical path delay (opd) and through-focus modular transfer function (MTF) curves for a 3.4 mm entrance pupil (EP) and the parameters of Table 2 are plotted in FIGS. 6A and 6B.

Accordingly, embodiments of the disclosure combine a base monofocal aspheric curvature with a MSPS structure to provide an extended range of functional vision at near and/or intermediate distances, while maintaining distance visual acuity and a safety profile similar to that of a typical monofocal IOL. Certain variants provide extended and continuous range of functional vision at near distances between 33 cm and 50 cm while maintaining distance visual acuity.

Combining a base aspherical monofocal lens with a MSPS structure as described herein may provide numerous advantages and benefits. For example, the image quality of the base lens at distance may begin dropping off in a well-controlled manner to an extent where the distance vision (e.g. visual acuity or contrast sensitivity) is still satisfying to patients. Moreover, as the image quality at distance drops off, the image quality at a range of intermediate/near defocus positions (e.g. 2-3D or 1.5-2.5D) may begin to increase, enabling patients to resolve targets at much wider focus range at intermediate/near distances.

Accordingly, while previous extended depth of focus (EDF) designs typically extend depth of focus from distance to intermediate distances, MSPS-enhanced designs described herein are capable of extending depth of focus around intermediate and near viewing distances (e.g., from 2D to 3D). And compared with previous monofocal designs where vision is corrected at two distinct points (near and far), MSPS-enhanced designs described herein extend depth of focus around intermediate or near viewing distances continuously (e.g., from 2D to 3D). As a result, the present disclosure addresses patient needs and benefits that are not addressed by prior EDF or monofocal lens designs.

Moreover, the MSPS technology described herein does not rely on discontinuous diffractive structures used in conventional EDF IOL designs. By eliminating discontinuous diffractive structures (which typically induce visual disturbances), disclosed lens designs may provide improved optical performance compared with conventional diffractive lenses. Similarly, the presently-described MSPS technology does not require small aperture or pinhole effects to extend depth of focus. Hence, the improved MSPS-enhanced lens designs contemplated herein can further improve optical performance by avoiding loss of light and improving efficiency relative to such existing designs. In addition, extra spherical aberration can be added on either the anterior or posterior surfaces of improved lenses disclosed herein to achieve optical distance vision at various pupil sizes, providing additional flexibility for customization of MSPS-enhanced lenses.

It will be appreciated that various of the above-disclosed and other features and functions, or alternatives thereof, may be desirably combined into many other different systems or applications. For example, although the above-described embodiments relate to ophthalmic lens is an IOL, one skilled in the art will appreciate that the MSPS features and techniques described herein are also applicable to soft or rigid contact lenses. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic lens, comprising
an optic comprising an anterior surface, a posterior surface, and an optical axis, at least one of the anterior surface and the posterior surface having a surface profile including:
a base curvature; and
a morphed sinusoidal phase shift structure modifying the base curvature along a portion of the surface profile, wherein the morphed sinusoidal phase shift structure comprises a plurality of morphed sinusoidal phase shift zones, wherein each of the plurality of morphed sinusoidal phase shift zones comprises a single sinusoidal period;
wherein the surface profile is defined as:

$$Z_{optic}(r) = Z_{base}(r) + Z_{MSPS}(r)$$

wherein $Z_{base}(r)$ defines the base curvature that is aspheric; and
$Z_{MSPS}(r)$ defines the plurality of morphed sinusoidal phase shift zones;

$$Z_{MPSS}(r) = M_i \frac{T_i^P}{\pi}\left(1 - \cos\left(\frac{r - R_i}{T_i^P}\pi\right)\right), R_i \leq r < R_i + T_i^P$$

$$Z_{MPSS}(r) = M_i \frac{T_i^P}{\pi}\left(1 - \cos\left(\frac{r - R_i - T_i^P}{R_{i+1} - R_i - T_i^P}\pi + \pi\right)\right),$$

$$R_i + T_i^P \leq r < R_{i+1}$$

and:
r denotes a radial distance from the optical axis in units of (mm);
$R_i$ and $R_{i+1}$ are starting and ending radial positions from the optical axis of each zone in units of (mm);
$M_i$ are step heights of each zone in units of (μm);
$T_i^P$ are critical points corresponding to a radial distance of a peak of each zone from the starting radial position of the zone; and
i indicates zone numbers i=0, 1, 2, 3 . . . , consecutively from the optical axis.

2. The ophthalmic lens of claim 1, wherein the morphed sinusoidal phase shift structure is configured to extend depth of focus of the ophthalmic lens as compared to an unmodified portion of the base curvature.

3. The ophthalmic lens of claim 1, wherein the morphed sinusoidal phase shift structure is configured to extend depth of focus of the ophthalmic lens to provide intermediate or near viewing distances in the range of 30-55 cm.

4. The ophthalmic lens of claim 1, wherein the morphed sinusoidal phase shift structure is configured to extend depth of focus of the ophthalmic lens to provide intermediate or near viewing distances in the range of 33-50 cm.

5. The ophthalmic lens of claim 1, wherein the morphed sinusoidal phase shift structure comprises at least seven morphed sinusoidal phase shift zones.

6. The ophthalmic lens of claim 1, wherein the ophthalmic lens comprises an intraocular lens.

7. The ophthalmic lens of claim 1, wherein the ophthalmic lens comprises a contact lens.

8. The ophthalmic lens of claim 1, wherein:

$$Z_{base}(r) = \frac{cr^2}{1 + \sqrt{1 - (1+k)c^2r^2}} + a_2r^2 + a_4r^4 + a_6r^6 + a_8r^8 + a_{10}r^{10}$$

and:
r denotes a radial distance from the optical axis in units of (mm);
c denotes a base curvature of the surface;
k denotes a conic constant;
$a_2$, $a_4$, $a_6$, $a_8$, and $a_{10}$ are, respectively, second, fourth, sixth, eighth, and tenth order coefficients.

9. The ophthalmic lens of claim 1, wherein the morphed sinusoidal phase shift structure comprises between 4 and 9 morphed sinusoidal phase shift zones.

10. The ophthalmic lens of claim 1, wherein each of the plurality of morphed sinusoidal phase shift zones comprises a step height different from a step height of an adjacent morphed sinusoidal phase shift zone.

* * * * *